(12) United States Patent
Davuluri et al.

(10) Patent No.: US 8,907,083 B2
(45) Date of Patent: Dec. 9, 2014

(54) PROCESS FOR THE PREPARATION, OF 2-(2-HYDROXYPHENYL)-BENZ [1, 3] OXAZIN-4-ONE AND ITS USE FOR PREPARATION OF 4-[3, 5-BIS (2-HYDROXYPHENYL)-IH-I, 2, 4-TRIAZOLTI-YL] BENZOIC ACID

(75) Inventors: Ramamohan Rao Davuluri, San Clemente, CA (US); Ravi Ponnaiah, Madurai (IN); Guruswamy Batthni, Hyderabad (IN); Chandra Murthy V. R. Medida, East Godavari (IN); Santhosh Dummu, Srikakulam (IN)

(73) Assignee: Ramamohan Rao Davuluri (IN)

( * ) Notice: Subject to any disclaimer, the term of this patent is extended or adjusted under 35 U.S.C. 154(b) by 9 days.

(21) Appl. No.: 13/819,452

(22) PCT Filed: Aug. 23, 2011

(86) PCT No.: PCT/IN2011/000560
§ 371 (c)(1),
(2), (4) Date: Feb. 27, 2013

(87) PCT Pub. No.: WO2012/025935
PCT Pub. Date: Mar. 1, 2012

(65) Prior Publication Data
US 2013/0338356 A1  Dec. 19, 2013

(30) Foreign Application Priority Data

Aug. 25, 2010  (IN) .......................... 2457/CHE/2010

(51) Int. Cl.
*C07D 265/22*  (2006.01)

(52) U.S. Cl.
CPC ................................ *C07D 265/22* (2013.01)
USPC ............... 544/92; 570/181; 564/463; 585/24

(58) Field of Classification Search
CPC ..................................................... C07D 265/22
USPC ........................................................... 544/92
See application file for complete search history.

(56) References Cited

PUBLICATIONS

Steinhauser et al. European Journal of Inorganic Chemistry Jan. 1, 2004, No. 21, pp. 4177-4192.*

* cited by examiner

*Primary Examiner* — Kahsay Habte
(74) *Attorney, Agent, or Firm* — Schmeiser, Olsen & Watts, LLP

(57) ABSTRACT

The invention provides a novel process for the synthesis of 2-(2-hydroxyphenyl)-benz[1,3]oxazin-4-one, the process comprising of reacting the salicylic acid with salicylamide in the presence of p-toluenesulfonyl chloride, base and solvent. The use of 2-(2-hydroxyphenyl)-benz[1,3]oxazin-4-one in the preparation of Deferasirox is also disclosed in the invention.

11 Claims, No Drawings

US 8,907,083 B2

PROCESS FOR THE PREPARATION, OF 2-(2-HYDROXYPHENYL)-BENZ [1, 3] OXAZIN-4-ONE AND ITS USE FOR PREPARATION OF 4-[3, 5-BIS (2-HYDROXYPHENYL)-IH-I, 2, 4-TRIAZOLTI-YL] BENZOIC ACID

FIELD OF THE INVENTION

The present invention is directed to a novel, industrially viable and cost effective process for manufacturing of 2-(2-hydroxyphenyl)-benz[1,3]oxazin-4-one which is a key intermediate in the synthesis of Deferasirox.

CROSS REFERENCE TO RELATED APPLICATION

This specification is the complete specification of and claims priority from the provisional application No 2457/CHE/2010 filed on 25 Aug. 2010

BACKGROUND OF THE INVENTION

4-[3,5-bis(2-hydroxyphenyl)-1H-1,2,4-triazol-1-yl]benzoic acid commonly known as Deferasirox is represented by Formula I.

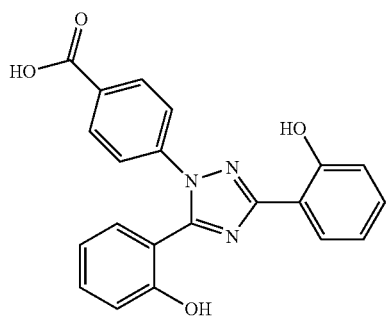 [SMILES: O=C(O)c1ccc(-n2nc(-c3ccccc3O)nc2-c2ccccc2O)cc1]

Deferasirox (exjade) is an iron chelating agent. Its main use is to reduce chronic iron overload in patients who are receiving long term blood transfusions for conditions such as beta-thalassemia and other chronic anemia's. It is a white to slightly yellow powder and it is practically insoluble in water and in an acid medium, the solubility increasing the pH.

Deferasirox was first disclosed in U.S. Pat. No. 6,465,504 by Novartis, and its process is as shown in scheme I. The process comprises reacting the salicylamide with salicyloyl chloride by heating at 170° C. provides 2-(2-hydroxyphenyl)-benz[e][1,3]oxazin-4-one, which is finally cyclized with 4-hydrazinobenzoic acid in refluxing ethanol.

Scheme I

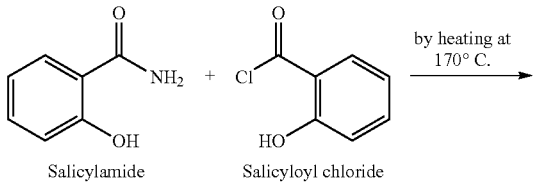

Salicylamide + Salicyloyl chloride — by heating at 170° C. →

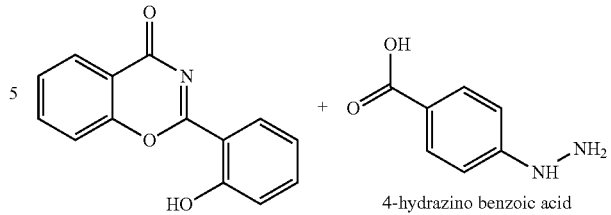

2-(2-hydroxyphenyl)-benz[e][1,3]oxazin-4-one + 4-hydrazino benzoic acid

Ethanol reflux ↓

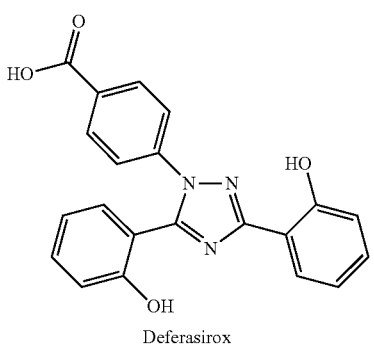

Deferasirox

WO2009094956 of Farmak describes the process for the preparation of Deferasirox as shown in scheme II below. The process comprises the condensation of 2-(2-hydroxyphenyl)-benz[1,3]-oxazine-4-one with 4-hydrazinobenzoic acid in the presence of organic acid or a mixture of organic acid and an organic solvent.

Scheme II

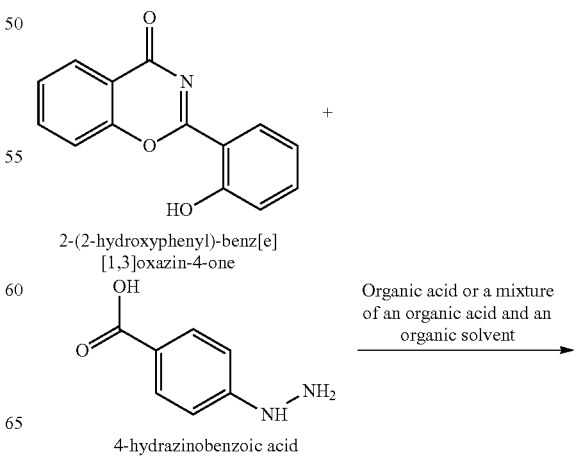

2-(2-hydroxyphenyl)-benz[e][1,3]oxazin-4-one + 4-hydrazinobenzoic acid

Organic acid or a mixture of an organic acid and an organic solvent →

3

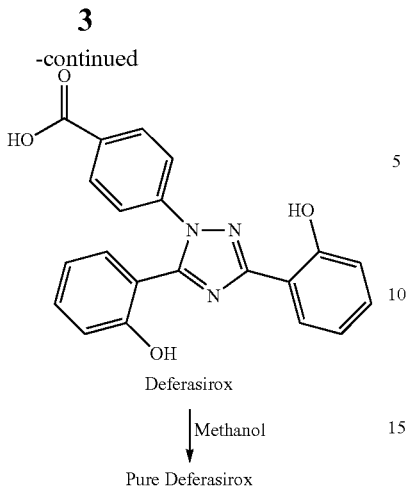

Deferasirox

↓ Methanol

Pure Deferasirox

WO2010023685 of Matrix describes the process for the preparation of Deferasirox as shown in scheme III. The process comprises the Salicylic acid reacted with thionyl chloride in the presence of solvent to give salicyloyl chloride, which is reacted with salicylamide to give 2-(2-hydroxyphenyl)-benz[1,3]-oxazine-4-one, then it is condensed with 4-hydrazino benzoic acid to give deferasirox.

4

The synthesis of Deferasirox described in earlier process, salicyloyl chloride is very unstable and particularly at higher temperature it will degrade gives impure product and low yields. Hence it is necessary to carried out the reaction at lower temperatures with solvent medium may gives better yield and desire purity. Therefore there is a continuing need for development of cost effective and industrially viable processes for manufacturing of Deferasirox.

SUMMARY OF THE INVENTION

The invention is a novel process for the synthesis of 2-(2-hydroxyphenyl)-benz[1,3]oxazin-4-one, the process comprising of reacting the salicylic acid with salicylamide in the presence of p-toluenesulfonyl chloride, base and solvent. The 2-(2-hydroxyphenyl)-benz[1,3]oxazin-4-one synthesized by the novel process is used in the preparation of Deferasirox.

The main object of the invention is to provide a novel process for the synthesis of 2-(2-hydroxyphenyl)-benz[1,3] oxazin-4-one.

Another object of the invention is to provide a process for producing 4-(3,5-bis(2-hydroxyphenyl)-1H-1,2,4-triazol-1-yl)benzoic acid (Deferasirox) employing the 2-(2-hydroxyphenyl)-benz[1,3]oxazin-4-one synthesized by the present invention.

Yet another object of the invention is to provide a process to get Deferasirox containing isopropyl alcohol as per ICH guidelines.

Scheme III

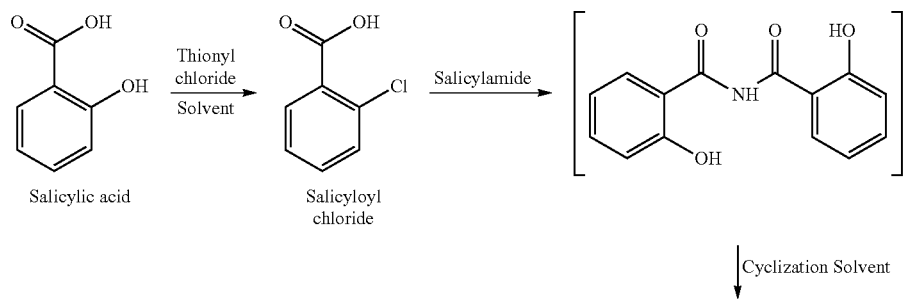

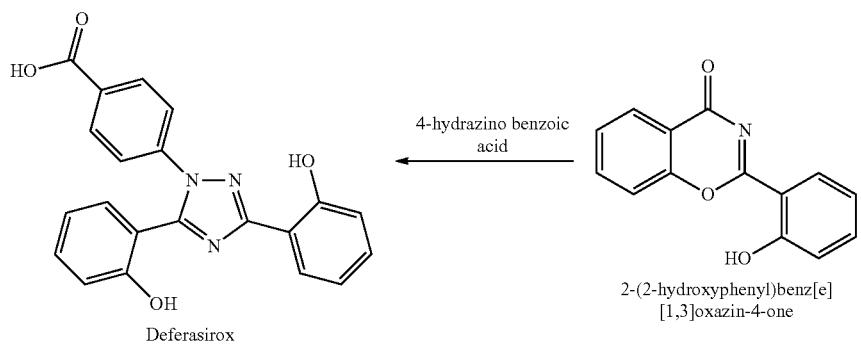

DESCRIPTION OF THE INVENTION

In accordance with the present invention 2-(2-hydroxyphenyl)-benz[1,3]oxazin-4-one is obtained by the reaction of salicylic acid with salicylamide in the presence of p-toulenesulfonyl chloride, base and solvent. The process of the invention is depicted in following scheme-IV.

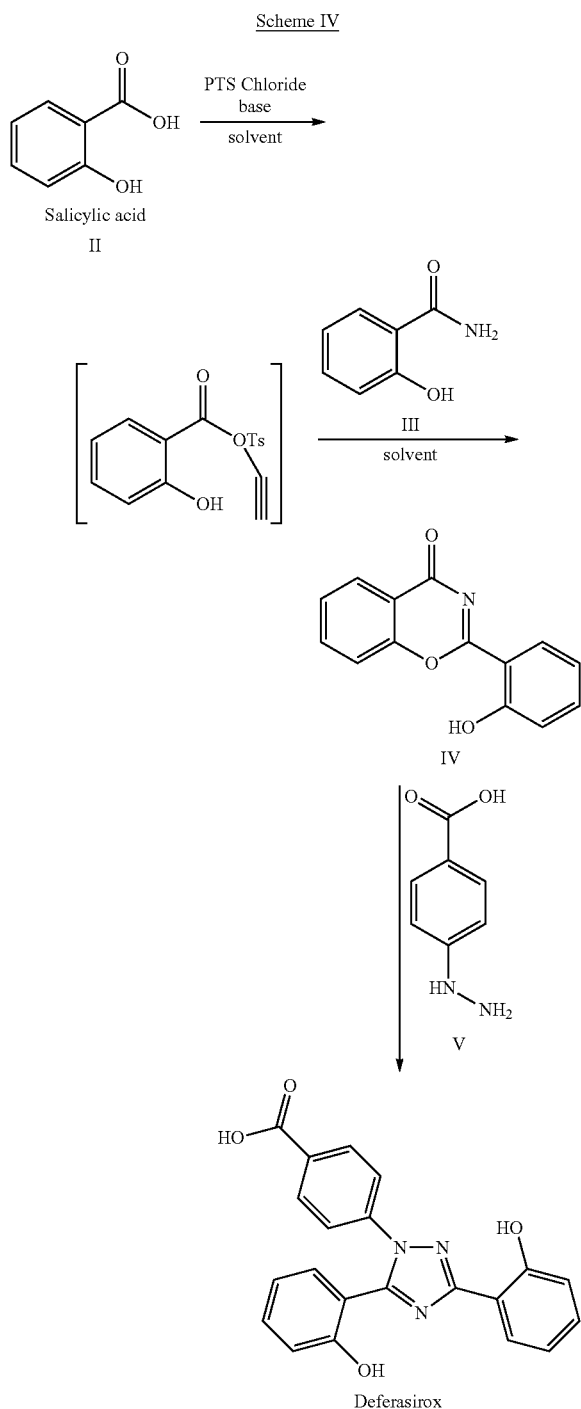

The process comprises:
a) reacting the salicylic acid of formula II with p-toulenesulfonyl chloride in the presence of organic base selected from the group of triethylamine, diisopropylethylamine, pyridine, diisopropyl amine, DBU and the like; preferably diisopropylethylamine or inorganic base like metal carbonates or metal bicarbonates or metal hydroxides, wherein the alkali metal carbonates is selected from the group sodium carbonate, potassium carbonate, metal bicarbonates like sodium bicarbonate, potassium bicarbonate, alkali hydroxide like sodium hydroxide, potassium hydroxide, lithium hydroxide and the like; preferably potassium carbonate and organic solvent selected from the group consisting of dichloromethane, THF, acetone and the like; preferably dichloromethane to obtain corresponding tosyl compound, which is obtained in situ reacted with salicylamide of compound of the formula III in the presence of solvent selected from the toluene, xylene, anisole, DMF, DMSO, chlorobenzene and the like; preferably toluene to obtain 2-(2-hydroxyphenyl)-benz[1,3]oxazin-4-one of formula IV.

b) condensation of compound of the formula IV with formula V in the presence of organic solvent selected from the group consisting of methanol, ethanol, propanol and the like; preferably methanol to obtain Deferasirox.

The present invention further involves a purification of Deferasirox comprising dissolving Deferasirox in IPA solvent and stir for sufficient period of time which will result in pure Deferasirox but IPA content in the product is very high about 15,000 to 20,000 ppm. In order to limit the IPA content compound taken into methanol and heated to reflux. After 4-5 hour content of IPA was found to be below 3000 ppm.

The invention is further illustrated with following non-limiting examples:

EXAMPLES

Example 1

Preparation of 2-(2-hydroxyphenyl)-benz[1,3]oxazin-4-one

A mixture of dichloromethane (200 ml), salicylic acid (50.0 gm) and p-toulenesulfonyl chloride (69 gm) were cooled to 10-15° C. Diisopropyl ethyl-amine (139.0 ml) was added drop-wise to the above mixture at 10-20° C. Reaction mass was stirred for 10 min at 10-20° C. and raised the temperature to 25-30° C. The reaction was maintained for 2 hours at 25-30° C. Reaction mass was cooled 0-5° C. Purified water (200 ml) was charged to the above mixture and stirred for 15 minutes. The layers were separated. Salicylamide (39.6 gm) and toluene (200.0 ml) were heated to 85-90° C. and the above organic layer was added drop-wise into salicyliamide solution with simultaneous distillation of solvent at 85-90° C. and distilled the solvent upto the reaction mass temperature reaches to 110-120° C. and further reaction was maintained for 3 hrs at 110-120° C. Further solvent was distilled under atmospheric pressure upto reaction mass temperature reaches to 140-160° C. and further the reaction was maintained for 1-2 hrs at 140-160° C. until the starting material disappears. Reaction mass was cooled to 75-80° C. and distilled off completely toluene under vacuum. Ethanol (50 ml) was added to the above reaction mass at 75-80° C. Reaction was stirred for 15 min and distilled off the ethanol at 75-80° C. Further ethanol (50.0 ml) was added stir for 5-10 min. Ethanol was distilled off completely under vacuum at 75-80° C. Ethanol (150 ml) was charged into above contents at 75-80° C. The contents were maintained for 1 hour at 75-80° C. and slowly cooled to 0-5° C. Reaction mass was maintained for 2 hrs at 0-5° C. The reaction mass was filtered and washed with ethanol (50.0 ml). Dried the compound at 50-55° C. Yield: 39.30%.

Example 2

Preparation of Deferasirox

A mixture of methanol (450.0 ml), 2-(2-hydroxyphenyl)-benz[1,3]oxazin-4-one (30.0 gm) were stir for 10 min at 25-30° C. To the above contents 4-hydrazino benzoic acid (20.03 gm) was added. The contents were heated to reflux temperature 65-70° C. The contents were maintained for 4 hours at 65-70° C. The reaction mass was cooled Slowly to 0-5° C. and maintained it for 1 hour at 0-5° C. The reaction mass was filtered and washed with methanol (30.0 ml). Compound was taken into methylene chloride and stir for 10 min 25-30° C. The contents were heated to reflux temperature (40-45° C.) and maintained the contents for 1 hr at reflux temperature. Cool the contents to 25-30° C. and stirred for 1 hr at 25-30° C. The reaction mass was filtered and washed with methylene chloride (30.0 ml). Dried the compound at 60-65° C. Yield: 79.0%.

Example 3

Purification of Deferasirox

Take Isopropyl alcohol (900.0 ml) and Deferasirox crude (30.0 gm) at 25-30° C. Stir the contents for 10 min at 25-30° C. Reaction mass was heated reflux temperature (80-85° C.) and maintained for 30 min at reflux temperature. Activated carbon (3.0 g) was added to the above reaction mass at reflux temperature. Reaction mass was maintained for 30 min at reflux temperature. The reaction mass was filtered through hyflow bed at hot condition and washed with isopropyl alcohol (30.0 ml). Isopropyl alcohol was distilled off until the 150 ml solvent is remained in the flask. Reaction mass was stirred for 30 min at 25-30° C. The mass was filtered and washed with isopropyl alcohol (30.0 ml). Methanol (150.0 ml) was added to the above wet compound and stirred for 10 min at 25-30° C. The contents were heated to reflux temperature (65-70° C.) and maintained the contents for 3 hr at reflux temperature. Reaction mass was cooled to 25-30° C. and stirred for 1 hr at 25-30° C. The reaction mass was filtered and washed with methanol (30.0 ml). Dried the compound at 60-65° C. Yield: 91.0%, Purity: >99.9%

We claim:

1. A process for the preparation of a 2-(2-hydroxyphenyl)-benz[e][1,3]oxazin-4-one compound of Formula-IV

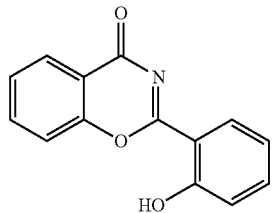

Formula-IV comprising the steps of:
a) reacting a salicylic acid compound of Formula-II:

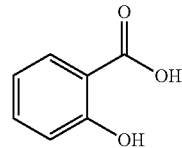

Formula-II with a p-toluenesulfonyl chloride in the presence of a base and an organic solvent to give a tosylated compound having the molecular structure

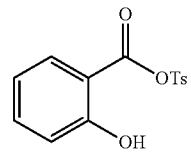 [SMILES: Cc1ccc(S(=O)(=O)OC(=O)c2ccccc2O)cc1]

b) combining said tosylated compound with a salicylamide compound of Formula-III represented by the molecular structure:

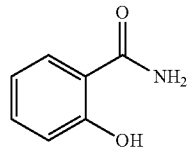

Formula-III in the presence of an organic solvent to give a 2-(2-hydroxyphenyl)benz[e][1,3]oxazin-4-one compound of Formula-IV.

2. The base as claimed in step (a) of the process according to claim 1, is selected from an organic base or an inorganic base.

3. The process according to claim 2, wherein the inorganic base is selected from alkali metal carbonates, metal bicarbonates or alkali hydroxides.

4. The process according to claim 3, wherein the alkali metal carbonates are selected from sodium carbonate or potassium carbonate.

5. The process according to claim 3, wherein the metal bicarbonates are selected from sodium bicarbonate or potassium bicarbonate.

6. The process according to claim 3, wherein the alkali hydroxides are selected from among sodium hydroxide, potassium hydroxide or lithium hydroxide.

7. The process according to claim 2, wherein the organic base is selected from the group consisting of trimethylamine, triethylamine, diisopropyl ethyl-amine, pyridine, diisopropyl amine and DBU.

8. The process according to claim 1, wherein the organic solvent used in step (a) is selected from any one of the members of the group consisting of dichloromethane, THF and acetone.

9. The process according to claim 1, wherein the organic solvent used in step (b) is selected from among any one of the members of the group of toluene, xylene, anisole, DMF, DMSO and chlorobenzene.

10. The process according to claim 1, wherein the reaction is carried out at a temperature between 25-160° C.

11. The process according to claim 10, wherein the reaction is carried out at the reflux temperature.

* * * * *

UNITED STATES PATENT AND TRADEMARK OFFICE
CERTIFICATE OF CORRECTION

| | | |
|---|---|---|
| PATENT NO. | : 8,907,083 B2 | Page 1 of 1 |
| APPLICATION NO. | : 13/819452 | |
| DATED | : December 9, 2014 | |
| INVENTOR(S) | : Ramamohan Rao Davuluri et al. | |

It is certified that error appears in the above-identified patent and that said Letters Patent is hereby corrected as shown below:

On the Title Page, Item (54) and in the Specification, Column 1, in the title,

Delete the "," after the first instance of the word "Preparation".

Replace the formula "4-[3,5-bis(2-hydroxyphenyl)-IH-I,2,4-triazoltI-yl]benzoic acid" with the formula "4-[3,5-bis(2-hydroxyphenyl)-1H-1,2,4-triazol-1-yl]benzoic acid".

Replace the formula "4-TRIAZOLTI-YL" with "4-TRIAZOL-1-YL".

Signed and Sealed this
Twenty-eighth Day of July, 2015

Michelle K. Lee
*Director of the United States Patent and Trademark Office*